(12) United States Patent
Young et al.

(10) Patent No.: US 8,242,398 B2
(45) Date of Patent: Aug. 14, 2012

(54) SWITCH FOR ULTRASONIC SURGICAL TOOL

(75) Inventors: Michael John Radley Young, Ashburton (GB); Stephen Michael Radley Young, Ashburton (GB)

(73) Assignee: SRA Developments Limited (GB)

( * ) Notice: Subject to any disclaimer, the term of this patent is extended or adjusted under 35 U.S.C. 154(b) by 282 days.

(21) Appl. No.: 12/664,252

(22) PCT Filed: Jun. 11, 2008

(86) PCT No.: PCT/GB2008/001994
§ 371 (c)(1),
(2), (4) Date: Apr. 26, 2010

(87) PCT Pub. No.: WO2008/152378
PCT Pub. Date: Dec. 18, 2008

(65) Prior Publication Data
US 2010/0258414 A1    Oct. 14, 2010

(30) Foreign Application Priority Data
Jun. 11, 2007    (GB) .................................... 0711151.1

(51) Int. Cl.
*H01H 13/08*    (2006.01)
(52) U.S. Cl. ...................... 200/332.2; 200/512; 200/505; 200/52 R; 606/42
(58) Field of Classification Search .................. 200/5 R, 200/17 R, 18, 52 R, 61.85, 61.86, 505, 511, 200/512, 517, 518, 293, 293.1, 329–332.2; 606/26, 34, 32, 38–42, 48, 50, 65–67, 80, 606/128, 169–174
See application file for complete search history.

(56) References Cited

U.S. PATENT DOCUMENTS
2,528,941 A    11/1950    Bassett at al.
(Continued)

FOREIGN PATENT DOCUMENTS
DE    24 60 481 A    12/1974
(Continued)

OTHER PUBLICATIONS
PCT Written Opinion of the International Searching Authority for Appln. No. PCT/GB2007/001968 filed May 25, 2007, European Patent Office.
(Continued)

*Primary Examiner* — Michael Friedhofer
(74) *Attorney, Agent, or Firm* — Carter, DeLuca, Farrell & Schmidt, LLP

(57) ABSTRACT

A switch unit (40) is mountable to a distal end of a handpiece of an electrically-activatable surgical tool, such as an ultrasonically-vibratable surgical tool. The switch unit (40) has a generally bullet-shaped outer form with an axial bore (42) through which a waveguide of the tool extends. A resiliently deformable band (1) extends around the switch unit (40) above a polygonal-section contact zone (2), such that fingertip pressure on the band (1) may locally depress the band (1) towards a flat area (12) of the contact zone (2). Switch contacts (11) are mounted to an inner surface of the band (1) opposite a plated circuit (10) located on each flat area (12) so as to form a plurality of switches. A switch to activate the tool is thus easily accessible to a user's fingertip in any orientation of the handpiece in the user's hand. The switch contacts (11) may each comprise a body having an electrical resistance dependent on a pressure exerted thereon. A magnitude of a response from the tool may thus be controlled by the pressure exerted by the user's fingertip.

15 Claims, 4 Drawing Sheets

U.S. PATENT DOCUMENTS

| | | | |
|---|---|---|---|
| 3,463,990 A | 8/1969 | Ross | |
| 3,565,062 A | 2/1971 | Kuris | |
| 3,657,056 A | 4/1972 | Winston et al. | |
| 3,746,814 A | 7/1973 | Lackey et al. | |
| 3,792,701 A | 2/1974 | Kloz et al. | |
| 3,861,391 A | 1/1975 | Antonevich et al. | |
| 4,144,646 A | 3/1979 | Takemoto et al. | |
| 4,188,952 A | 2/1980 | Loschilov et al. | |
| 4,243,388 A * | 1/1981 | Arai | 433/27 |
| 4,248,232 A | 2/1981 | Engelbrecht et al. | |
| 4,492,832 A * | 1/1985 | Taylor | 200/52 R |
| 4,832,683 A | 5/1989 | Idemoto et al. | |
| 5,019,083 A | 5/1991 | Klapper et al. | |
| 5,151,099 A | 9/1992 | Young et al. | |
| 5,167,619 A | 12/1992 | Wuchinich | |
| 5,322,055 A | 6/1994 | Davison et al. | |
| 5,324,297 A | 6/1994 | Hood et al. | |
| 5,324,299 A | 6/1994 | Davison et al. | |
| 5,330,481 A | 7/1994 | Hood et al. | |
| 5,413,107 A | 5/1995 | Oakley et al. | |
| 5,439,217 A * | 8/1995 | Ganger, Sr. | 473/202 |
| 5,451,735 A * | 9/1995 | Worthington et al. | 200/505 |
| 5,520,678 A | 5/1996 | Heckele et al. | |
| 5,549,544 A | 8/1996 | Young et al. | |
| 5,656,015 A | 8/1997 | Young | |
| 5,695,510 A | 12/1997 | Hood | |
| 5,749,877 A | 5/1998 | Young | |
| 5,769,211 A | 6/1998 | Manna et al. | |
| 5,873,873 A | 2/1999 | Smith et al. | |
| 5,885,301 A | 3/1999 | Young | |
| 5,935,143 A | 8/1999 | Hood et al. | |
| 6,004,335 A | 12/1999 | Vaitekunas et al. | |
| 6,056,735 A | 5/2000 | Okada et al. | |
| 6,129,735 A | 10/2000 | Okada et al. | |
| 6,283,981 B1 | 9/2001 | Beaupre | |
| 6,291,466 B1 | 9/2001 | Gwon et al. | |
| 6,425,906 B1 | 7/2002 | Young et al. | |
| 6,891,118 B2 * | 5/2005 | Wecke et al. | 200/518 |
| 6,971,994 B1 | 12/2005 | Young et al. | |
| 7,112,199 B2 * | 9/2006 | Cosmescu | 606/45 |
| 7,285,117 B2 * | 10/2007 | Krueger et al. | 606/34 |
| 7,306,592 B2 * | 12/2007 | Morgan et al. | 606/32 |
| 7,507,925 B2 * | 3/2009 | Rudolf et al. | 200/332.2 |
| 2002/0046938 A1 | 4/2002 | Donofrio et al. | |
| 2002/0049464 A1 | 4/2002 | Donofrio et al. | |
| 2002/0099400 A1 | 7/2002 | Wolf et al. | |
| 2004/0044356 A1 | 3/2004 | Young et al. | |
| 2005/0021065 A1 | 1/2005 | Yamada et al. | |
| 2005/0177184 A1 | 8/2005 | Easley | |
| 2006/0100548 A1 | 5/2006 | Ferguson | |
| 2008/0255483 A1 * | 10/2008 | Goldberg | 601/72 |

FOREIGN PATENT DOCUMENTS

| | | |
|---|---|---|
| EP | 0 619 993 A1 | 10/1994 |
| EP | 0617935 | 10/1994 |
| EP | 0 646 435 A1 | 4/1995 |
| EP | 0 970 659 A1 | 1/2000 |
| EP | 0970660 A1 | 1/2000 |
| EP | 1138264 A1 | 10/2001 |
| EP | 1 229 515 A2 | 8/2002 |
| EP | 1 625 836 | 2/2006 |
| EP | 1 693 027 A | 8/2006 |
| FR | 2749501 | 12/1997 |
| GB | 2277448 | 11/1994 |
| GB | 2288120 | 10/1995 |
| GB | 2333709 | 8/1999 |
| GB | 2333709 A | 8/1999 |
| GB | 2 365 775 A | 2/2002 |
| GB | 2425480 A | 11/2006 |
| GB | 2 428 283 A | 1/2007 |
| SU | 1388002 A1 | 4/1988 |
| WO | WO 91/11965 | 8/1991 |
| WO | WO 92/22259 | 12/1992 |
| WO | WO 99/35982 | 7/1999 |
| WO | WO 99/52489 | 10/1999 |
| WO | WO 01/21079 A1 | 3/2001 |
| WO | WO 02/38057 | 5/2002 |
| WO | WO 03/047769 | 6/2003 |
| WO | WO 03/082132 A1 | 10/2003 |
| WO | WO 03082133 | 10/2003 |
| WO | WO 2005/084553 | 9/2005 |
| WO | WO 2006/008502 | 1/2006 |
| WO | WO 2006/020803 | 2/2006 |
| WO | WO 2006/052498 | 5/2006 |
| WO | WO 2006/059120 | 6/2006 |
| WO | WO 2006/092576 | 9/2006 |
| WO | WO 2007/138295 | 12/2007 |
| WO | WO 2008/065323 | 6/2008 |

OTHER PUBLICATIONS

PCT International Search Report dated Sep. 12, 2007 for Appln. No. PCT/GB2007/001968 filed May 25, 2007.

PCT International Search Report for PCT/GB2007/003560 filed Sep. 18, 2007, dated Jan. 3, 2008.

GB Search Report for GB 0718476.5 dated Nov. 29, 2007.

PCT International Preliminary Report on Patentability for PCT/GB2007/003560 filed Sep. 18, 2007, dated Mar. 24, 2009.

PCT International Preliminary Report on Patentability for PCT/GB2006/000697 filed Feb. 28, 2006, dated Sep. 11, 2007.

International Search Report for PCT/GB2006/000697 dated May 3, 2006.

GB Search Report dated Jun. 27, 2006 for GB0504321.1.

PCT International Search Report dated May 28, 2008 for PCT/GB2008/000588.

* cited by examiner

SWITCH FOR ULTRASONIC SURGICAL TOOL

This application claims priority to PCT International Application PCT/GB2008/001994 filed on Jun. 11, 2008 which was published on Dec. 18, 2008 as Publication No. WO 2008/152378 A2. The PCT application claims priority to a patent application filed on Jun. 11, 2007 in Great Britain and assigned Patent Application No. GB0711151.1. The entire content of these applications is incorporated herein by reference.

The present invention relates to a switching mechanism for activating a surgical tool, such as tools used for minimally invasive surgery (MIS). More particularly, but not exclusively, it relates to a switch system for use with a laparoscopic ultrasonic surgical tool.

Historically, ultrasonically-energised tools, and other electrically activated surgical devices that are activated during surgery to conduct a procedure, have had at least one common problem to address: the provision of activating means that may easily be contacted by a user's digits without compromising any aspect of the surgery. This is particularly useful in cases in which handling the tool may require twisting or angular movements of the hand-joints or fingers, in order to place and hold the tool in a desired position before activation. For example, while performing a small internal incision, it is of the highest importance to place an activatable distal end of the tool in the correct position so that the user may ensure that it acts on the desired target tissue. The user will often need simultaneously to manipulate a laparoscope positioned to show the target tissue and to manipulate the surgical tool, while viewing a monitor displaying the view captured by the laparoscope.

There is hence a need for a surgical tool that will provide maximum ease of manipulation to position the tool as desired, while permitting easy access to activating means of the tool in any alignment of the tool in the user's hand.

It is known to provide such a surgical tool with a pistol-like butt comprising a trigger switch operable to activate the tool once the cutting tip of the tool is positioned and held in the desired position. The problem with this arrangement is that the user may well be restricted in his hand movements. The butt may interfere with the user's hand movements, restricting rotational motions which may be required for delicate surgery, and the trigger switch may not be conveniently positioned for the user's fingers when the tool is correctly positioned.

Accordingly, while trying to position the tool, judging by the feedback being monitored from the laparoscope, the surgeon may have to make an uncomfortable twist or even use help from the hand holding the laparoscope in order to achieve the correct position. This may in turn affect the optimum view being captured by the laparoscope.

It is therefore an object of the present invention to provide manual activation arrangements for a laparoscopic surgical tool or the like allowing activation in a range of hand positions, particularly should complex hand movements be required to position the tool before activation to carry out a surgical procedure.

According to a first aspect of the present invention, there is provided a switch unit so mountable to a distal end of a handpiece of an activatable surgical tool as to be contactable by a finger of a hand manipulating the handpiece, wherein the switch unit is generally radially symmetrical and comprises a plurality of first digitally-operable switch means arranged around a circumference thereof, operation of any one of which is adapted to activate the tool.

Preferably, the switch unit is provided with an axially-extending bore adapted for passage of a shaft of the tool therethrough.

Said shaft may comprise a waveguide of an ultrasonically-vibratable surgical tool.

The switch unit may comprise a generally frustoconical body having said plurality of first switch means mounted thereto.

Preferably, the switch unit comprises at least one second digitally-operable switch means disposed between a distal end of the switch unit and the first switch means.

Said second switch means may be adapted to activate a different function of the tool to that activated by the first switch means.

In a preferred embodiment, each said switch means comprises resiliently flexible cover means spaced in an "off" configuration of the switch means from contact means thereof, said cover means being deflectable by digital pressure into contact with said contact means in an "on" configuration of the switch means.

A single common cover means may provided for all said first switch means.

The switch unit may be provided with a plurality of recess means, one said switch means being disposed within each said recess means.

A plurality of said first recess means may be arranged contiguously around a circumference of the switch unit, each first recess means containing a respective first contact means.

Each contact means preferably comprises a body of a material having an electrical resistance dependent on a pressure exerted thereon.

The switch means may then be adapted to provide an activation signal dependent on a digital pressure exerted thereon.

According to a second aspect of the present invention, there is provided a handpiece for an electrically activatable surgical tool comprising a switch unit as described in the first aspect above, operatively mounted to a distal end of said handpiece.

An embodiment of the present invention will now be more particularly described by way of example and with reference to the accompanying drawings, in which.

Figure 1:
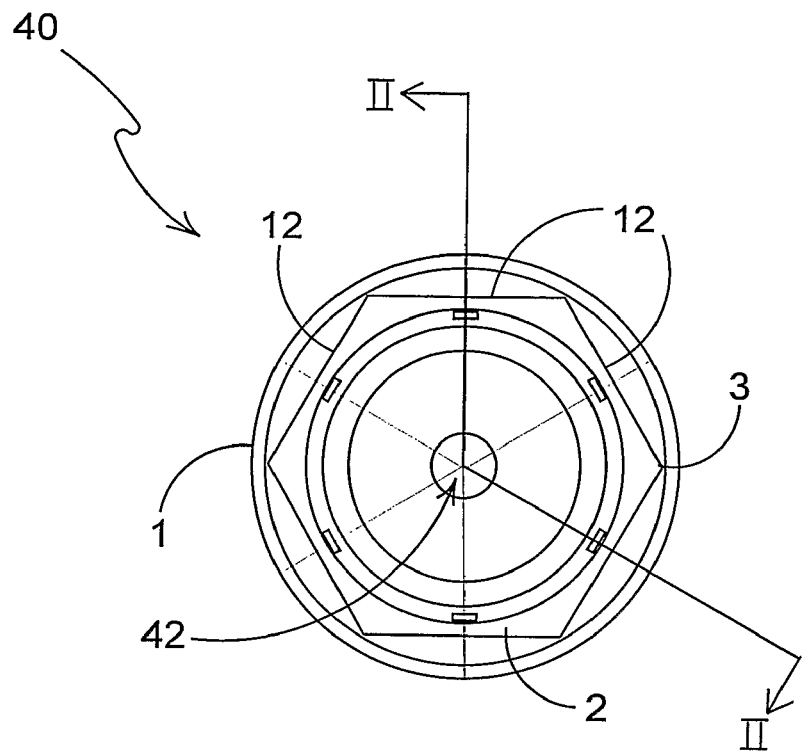
FIG. 1 is a radial cross-section, taken along line I-I of FIG. 2, of a switch head embodying the present invention.
Figure 2:
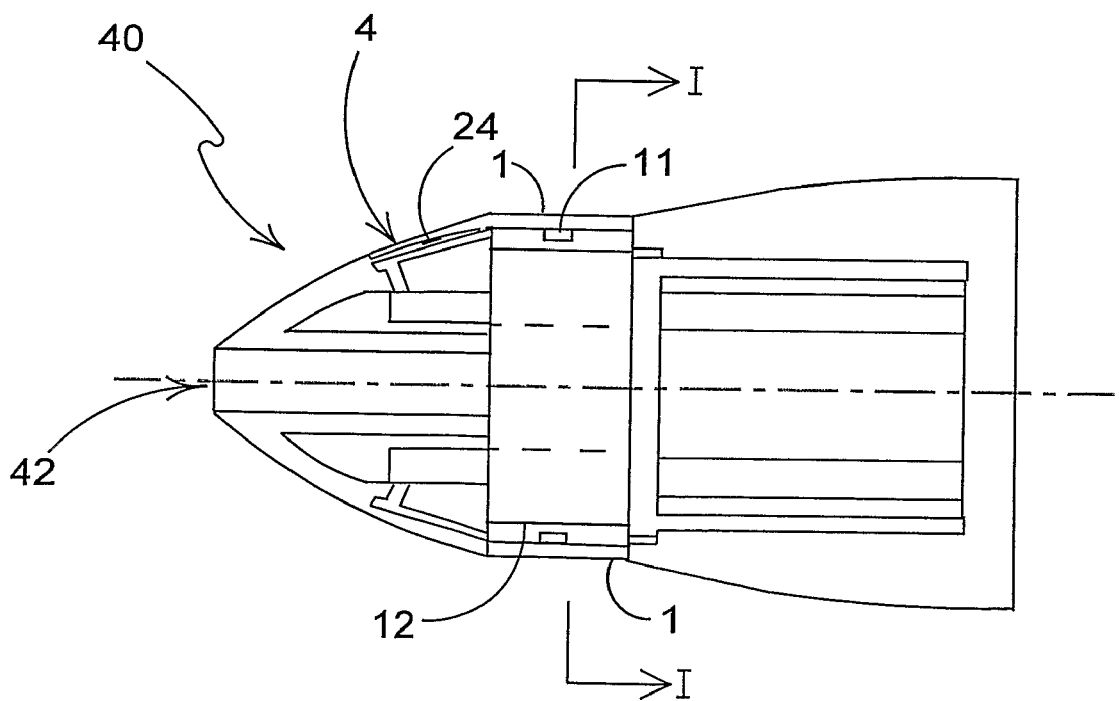
FIG. 2 is a transverse cross-section, taken along line II-II of FIG. 1, of the switch head shown in FIG. 1.

Referring to now to the Figures, and to FIGS. 1 and 2 in particular, a switch head 40 has a generally bullet-shaped radially-symmetrical form, and is detachably mountable to a distal end of a handpiece of an ultrasonically-vibratable surgical tool (not shown). The switch head 40 is provided with an axial bore 42, through which an elongate waveguide of the tool extends (not shown for clarity).

Figure 6:
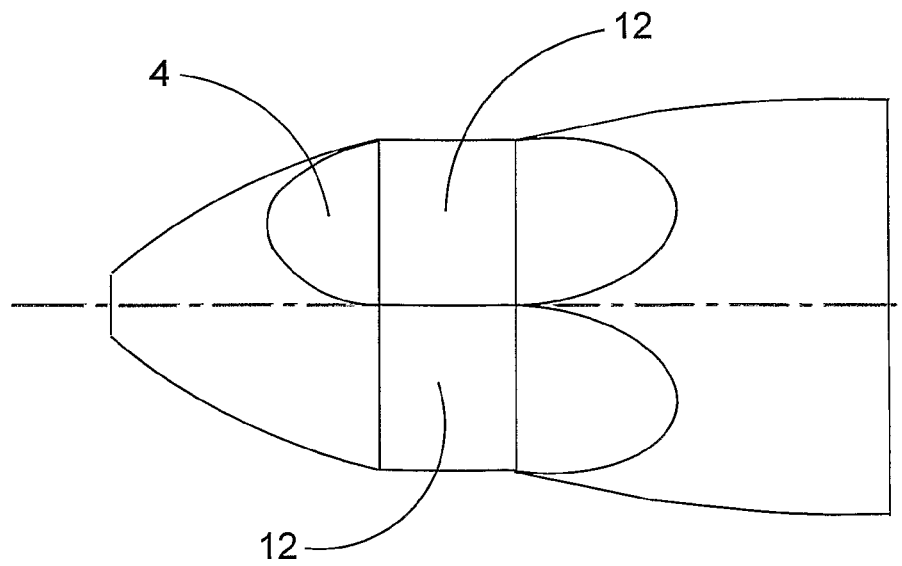
FIG. 6 is a schematic side elevation of the switch head shown in FIG. 1.

The switch head 40 comprises a resiliently-deformable band 1 of an elastomeric material extending circumferentially around a waist portion of the switch head 40. A regularly-spaced array of six main switches is arranged circumferentially around the switch head 40 beneath this band 1. A contact zone 2 of the switch head 40 beneath the band 1 has a hexagonal outer profile and a circular inner profile, arranged such that it contacts the band 1 supportingly at apical, thicker portions 3. The band 1 may thus be depressed by a user's finger towards and into contact with any of the flat outer faces 12 of the contact zone 2, while the band 1 as a whole maintains its shape. A first switch contact 11 is mounted to the inner face of the contact zone 2 beneath each flat outer face 12 thereof. FIG. 6 shows the flat faces 12 with the band 1 removed.

A side-lobe of the deformable band 1 extends distally from its circumferential portion, covering a recess 4 in the switch head 40 (see also FIG. 6), mounted beneath an inner face of which is a second switch contact 24.

Figure 3:
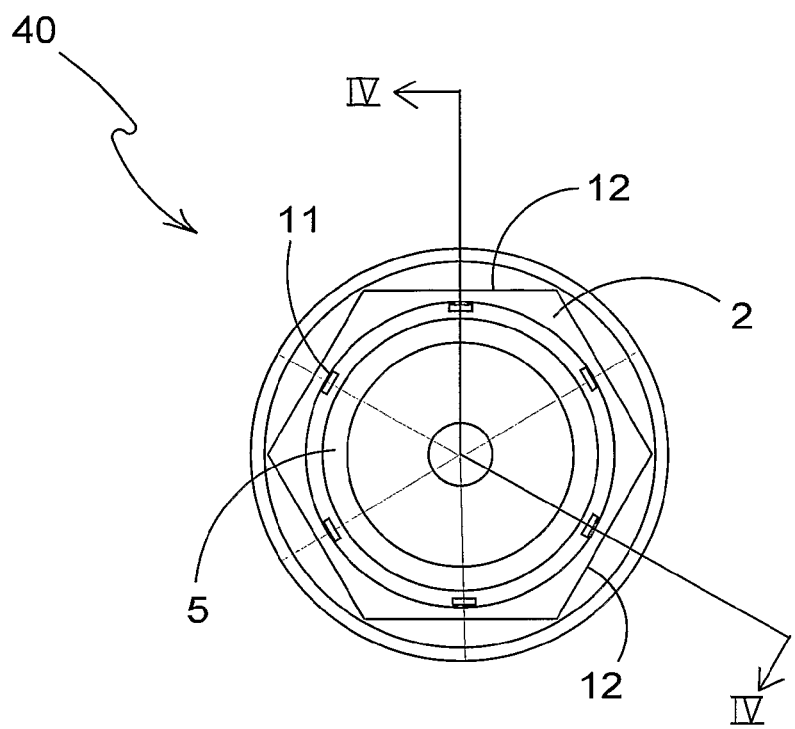
FIG. 3 is a radial cross-section, taken along the line IV-IV of FIG. 4, of the switch head shown in FIG. 1.
Figure 4:
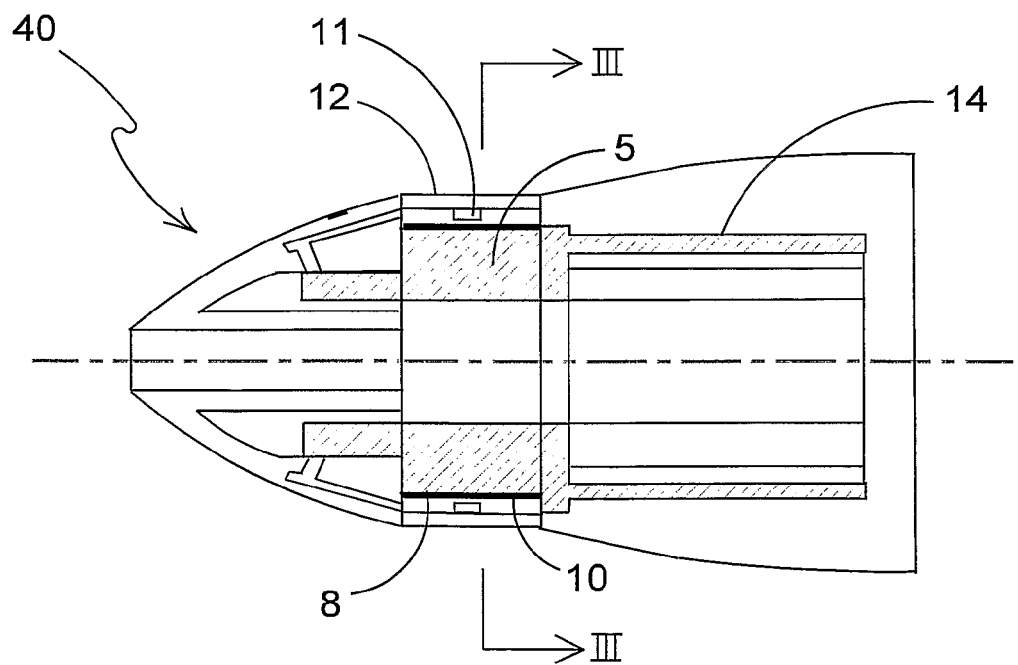
FIG. 4 is a transverse cross-section taken along the line III-III of FIG. 3, of the switch head shown in FIG. 1, illustrating in particular an internal mounting body thereof.
Figure 5:
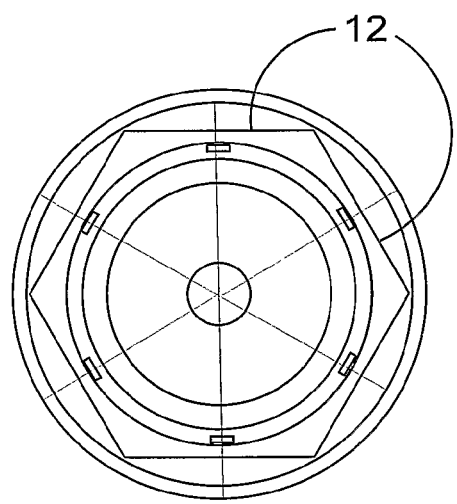
FIG. 5 is a radial cross-section, taken along line V-V of FIG. 6, of the switch head shown in FIG. 1.
Figures 7, 8:
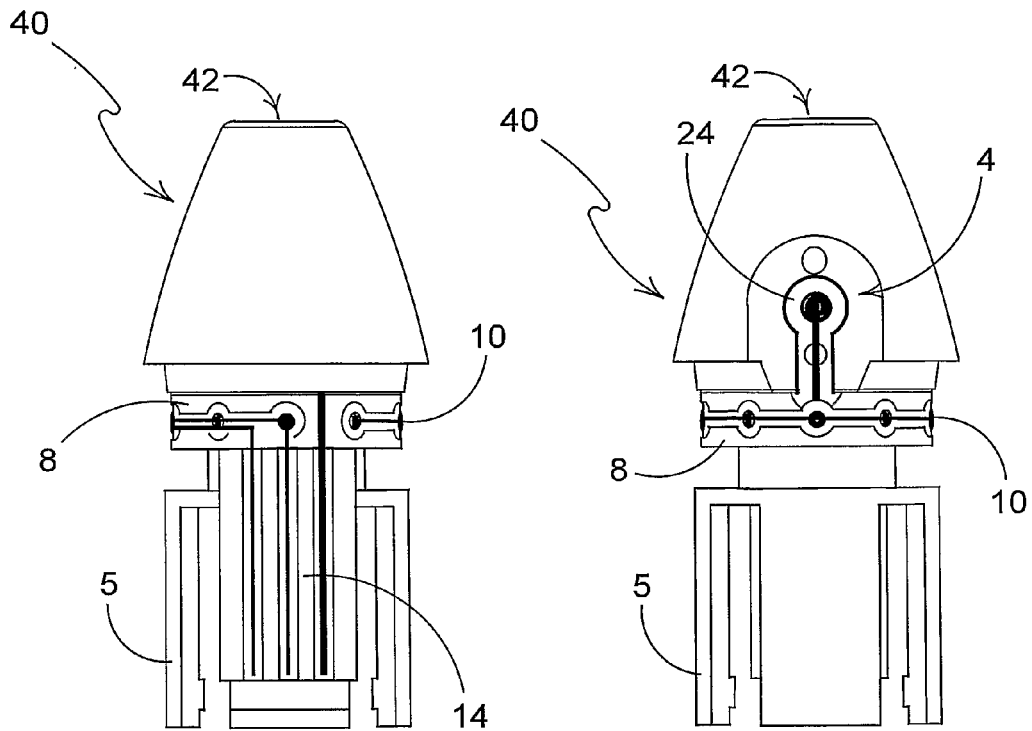
FIGS. 7, 8 and 9 are respectively top, bottom and side elevations of the switch head shown in FIG. 1, partially disassembled to reveal contact elements and electrical circuit arrangements thereof.
Figure 9:
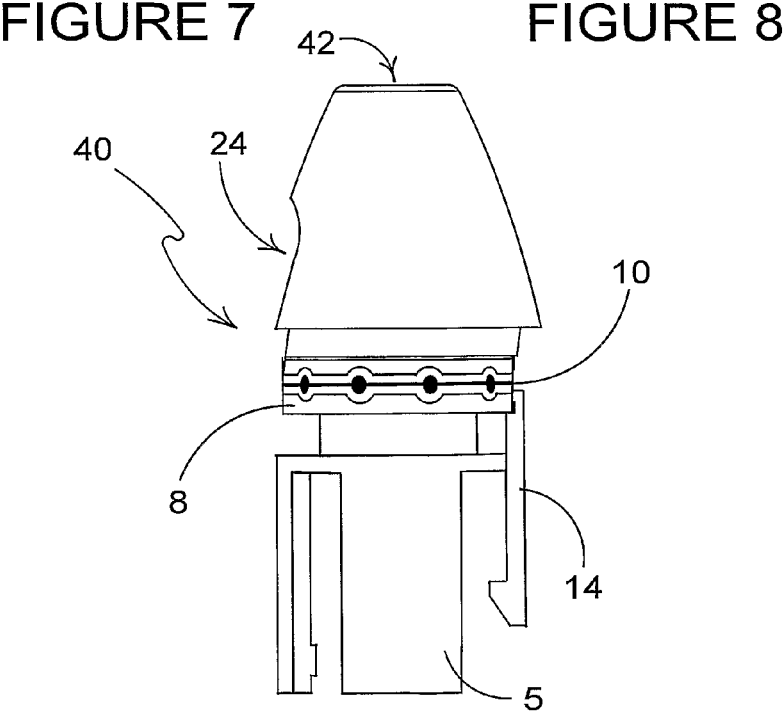

Referring now to FIGS. 3 and 4, a generally radially-symmetrical rigid plastics mounting body 5 is located coaxially within the switch head 40. A cylindrical outer surface 8 of the mounting body 5 adjacent the contact zone 2 of the switch head 40 is provided with a plurality of plated circuits 10, each of which opposes a respective switch contact 11. A similar arrangement of plated circuits (not shown in FIGS. 3 and 4) is provided adjacent the recess 4 and second switch contact 24. The circuits 10 are preferably gold-plated and of a pin-in-socket configuration (see FIGS. 7 to 9).

Thus, when a portion of the band 1 above a flat face 12 of the contact zone 2 is depressed by a finger of a user of the handpiece, it will deform into contact with the flat face 12. The finger pressure will bow the flat face 12 slightly inwardly, such that the respective switch contact 11 meets its corresponding plated circuit 10. This makes the circuit 10. Each of the circuits 10 is operatively linked, through a metal-plated elongate interconnect element 14 extending proximally from the mounting body 5, to the handpiece. The signal produced when any of the circuits 10 is made will activate the surgical tool, for example activating the ultrasound generator of an ultrasonically-vibratable laparoscopic implement. Release of the band 1 allows the respective flat face 12 to revert to being flat, displacing the contact switch 11 out of contact and inactivating the tool once more.

Thus, whatever the angular position of the tool in the user's hand, the user will be able to press on a portion of the band 1 convenient to his finger in order to activate the tool, without needing to adjust the position of the tool in his hand. More or less than six faces 12 are possible, but six is effective and convenient. The operation of the second switch 4, 24 may be analogous or may be of a more conventional form. The second switch may be linked to a activation of a different function of the tool, or may be used as an additional on-off switch.

In a preferred embodiment, the switch contacts 11, 24 each comprise a pellet of a material whose electrical resistance depends on the pressure exerted thereon. Conductive carbon "pills" or QTC (quantum tunnelling composite) elements are examples of these. When such a switch contact 11, 24 is employed, not only is there a make/break contact to activate or inactivate the tool, but the digital pressure exerted by the user on the band 1 will affect the resistance of the switch contact 11, 24 and hence the magnitude of the resultant signal passed on to the handpiece. This can be used to control the magnitude of the activation of the tool—e.g. the amplitude of the ultrasonic energy emitted by the generator in the handpiece of an ultrasonically-vibratable tool.

The switch head 40 may be detachable from the handpiece for cleaning. Alternatively, it would be a disposable item, replaced for each surgical procedure.

The invention claimed is:

1. A switch unit so mountable to a distal end of a handpiece of an activatable surgical tool as to be contactable by a finger of a hand manipulating the handpiece, said switch unit being radially symmetrical and having an intermediate waist portion, wherein the waist portion comprises an inner deformable member having in transverse cross-section an outer profile comprising a plurality of flat surfaces and at least one apex and an inner profile defining a channel therethrough and having one or more first switch contacts mounted or affixed thereto such that a first switch contact is mounted or affixed opposite each flat surface; and an outer deformable member extending circumferentially around the waist portion, which, in an undeformed state, contacts the inner deformable member only at the or each apex, wherein, in use, pressure applied by a finger deforms the outer deformable member to exert a force on the inner deformable member at a location remote from the or each apex such that each first switch contact moves in an inward direction towards a corresponding second switch contact located within the channel, thereby activating the tool.

2. A switch unit as claimed in claim 1, wherein the channel is adapted for passage of shaft means of the tool therethrough.

3. A switch unit as claimed in claim 1, which is generally frustoconical in shape.

4. A switch unit as claimed in claim 1, further comprising at least one secondary switch means located between a distal end of the switch unit and the intermediate waist portion.

5. A switch unit as claimed in claim 4, wherein said secondary switch means is adapted to activate a different function of the tool from that activated by the inward movement of the first switch contact means towards the corresponding second switch contact means located within the channel.

6. A switch unit as claimed in claim 1, further comprising a cover means over the outer deformable member.

7. A switch unit as claimed in claim 1, wherein each first switch contact comprises a body of material having an electrical resistance dependent on a pressure exerted thereon.

8. A switch unit as claimed in claim 7, wherein the body of material comprises a conductive carbon "pill" or quantum tunnelling composite element.

9. A switch unit as claimed in claim 1, wherein the corresponding second switch contact comprises a plated circuit.

10. A switch unit as claimed in claim 1, wherein the or each first switch contact is adapted to provide an activation signal dependent on a digital pressure exerted thereon.

11. A switch unit as claimed in claim 1, wherein the inner deformable member has in transverse cross-section an outer profile comprising six flat surfaces.

12. A handpiece for an electrically activatable surgical tool comprising a switch unit as claimed in claim 1 operatively mounted to a distal end of said handpiece.

13. A handpiece as claimed in claim 12, wherein the surgical tool is an ultrasonically-vibratable surgical tool.

14. A handpiece as claimed in claim 12, wherein the channel is adapted for the passage therethrough of an elongate waveguide of the ultrasonically-vibratable surgical tool.

15. An electrically activatable surgical tool comprising a switch unit as claimed in claim 1.

* * * * *